United States Patent [19]

Lysenko et al.

[11] Patent Number: 5,414,130

[45] Date of Patent: May 9, 1995

[54] PROCESS FOR THE PREPARATION OF DIAMINORESORCINOL

[75] Inventors: Zenon Lysenko; Richard G. Pews; Paul Vosejpka, all of Midland, Mich.

[73] Assignee: The Dow Chemical Company, Midland, Mich.

[21] Appl. No.: 173,547

[22] Filed: Dec. 23, 1993

[51] Int. Cl.$^6$ .............................................. C07C 209/36
[52] U.S. Cl. ...................................... 564/418; 564/423
[58] Field of Search ...................... 564/418, 423, 417

[56] References Cited

U.S. PATENT DOCUMENTS

| | | | |
|---|---|---|---|
| 4,087,410 | 5/1978 | Dominianni | 568/766 |
| 4,766,244 | 8/1988 | Lysenko | 564/418 |
| 4,912,246 | 3/1990 | Lysenko et al. | 558/269 |
| 5,001,279 | 3/1991 | Yin | 568/709 |
| 5,072,053 | 12/1991 | Blank | 568/586 |
| 5,272,143 | 12/1993 | Benson | 514/215 |

OTHER PUBLICATIONS

"Hydroxylation of Nitroarenes with Alkyl Hydroperoxide Anions via Vicarious Nucleophilic Substitution of Hydrogen" by Mieczyslaw Makosza et al. listed in The Journal of Organic Chemistry vol. 55, No. 17 © 1990 American Chemical Society.

"Preparation of 1,3-dihydroxy-4,6-diaminobenzene as material for poly(benzbisoxazoles" by Sato Tetsuo et al listed in Chemical Abstracts, vol. 112 (1990).

"Preparation of 1,3-dihydroxy-4,6-diaminobenzene and Its Salts" by Kato Kazufumi et al. listed in Chemical Abstracts vol. 113. (1990).

"Preparation of 1,3-dihydroxy-4,6-diaminobenzene of Its Salts as Materials for Poly(benzobisoxazoles" by Kato Kazufumi et al. listed in Chemical Abstracts vol. 114 (1991).

"Preparation of 4,6-dinitroresorcinol from 1,5-dichloro-2,4-dinitrobenzens" by Rauner Wolfram et al listed in Chemical Abstracts vol. 70 (1968).

"Dealkylation of Activated Alkyl Aryl Ethers Using Lithium Chloride in Dimethylformamide" by Angela M. Bernard et al. listed in Communications (Apr. 1989 issue).

"Boron Trihalide-Methyl Sulfide Complexes as Convenient Reagents For Dealkylation of Aryl Ethers" by Paul G. Williard et al. listed in Tetrahedron Letters vol. 21, pp. 3731-3734 (1980).

Primary Examiner—Glennon H. Hollrah
Attorney, Agent, or Firm—Lynn M. Zettler

[57] ABSTRACT

A method of producing 4,6-diaminoresorcinol comprising a) reducing a dinitroarylether of the formula:

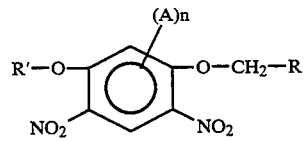

wherein R is hydrogen, $C_1$-$C_6$ alkyl, cycloalkyl or $CH=CH_2$, R' is hydrogen or $CH_2$—R, each A is independently Cl, Br, or I, and n is 0, 1 or 2; to form a diaminoarylether, and b) cleaving the ether group(s) from the diaminoarylether under conditions such that 4,6-diaminoresorcinol is formed as a salt or other stabilized form thereof.

16 Claims, No Drawings

PROCESS FOR THE PREPARATION OF DIAMINORESORCINOL

BACKGROUND OF THE INVENTION

The present invention relates to a method for the preparation of diaminoresorcinol.

4,6-Diaminoresorcinol is a monomer used in preparing polybenzoxazoles (PBO). Although there are a number of known methods for preparing 4,6-diaminoresorcinol, there continues to be a need to find more efficient and cost effective routes to obtain 4,6-diaminoresorcinol.

One known method involves synthesizing the monomer from 1,2,3-trichlorobenzene as described in U.S. Pat. No. 4,766,244 issued to Lysenko. However, 1,2,3-trichlorobenzene has limited availability.

Another method for preparing 4,6-diaminoresorcinol involves treating 1,3-dichloro-4,6-dinitrobenzene with base, to form 4,6-dinitroresorcinol. Although 4,6-dinitroresorcinol may be reduced to form 4,6-diaminoresorcinol, the product recovery is prohibitively low for commercial value.

In yet another method, the appropriate arylether such as di-arylmethoxy-dinitrobenzene can be cleaved to produce 4,6-diaminoresorcinol. U.S. Pat. No. 5,072,053, issued to Blank et al., describes cleaving arylethers by converting di-arylmethoxydinitrobenzenes to 4,6-diaminoresorcinol by catalytic reduction using a platinum metal supported catalyst, which cleaves the diethers and reduces the nitro groups to amines. However, the method also produces toluene as an unwanted by-product which must be removed or converted back to benzyl alcohol for recycle.

Accordingly, it remains highly desirable to provide an efficient and cost effective method for producing 4,6-diaminoresorcinol which does not have the foregoing disadvantages.

SUMMARY OF THE INVENTION

The present invention is a method for preparing 4,6-diaminoresorcinol comprising a) reducing a dinitroarylether of the formula:

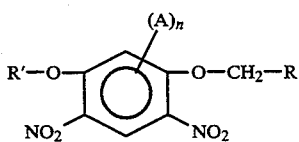

wherein R is hydrogen, $C_1-C_6$ alkyl, cycloalkyl or $CH=CH_2$, R' is hydrogen or $CH_2-R$, each A is independently Cl, Br, or I, and n is 0, 1 or 2; to form a diaminoarylether, and b) cleaving the ether group(s) from the diaminoarylether under conditions such that 4,6-diaminoresorcinol is formed as a salt or other stabilized form thereof.

The preferred dinitroarylethers advantageously employed in the method of the present invention correspond to the formula:

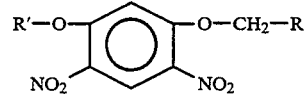

wherein R is hydrogen, $C_1-C_6$ alkyl, cycloalkyl, or $CH=CH_2$ and R' is hydrogen or $CH_2-R$.

In a preferred embodiment of the present invention 5-methoxy-2,4-dinitrophenol is converted to 4,6-diaminoresorcinol by contacting 5-methoxy-2,4-dinitrophenol with hydrogen in the presence of a palladium on carbon catalyst followed by hydrochloric acid.

Using the process of the present invention, an efficient, cost effective alternative route to 4,6-diaminoresorcinol is achieved.

DETAILED DESCRIPTION OF THE INVENTION

Dinitroarylethers appropriate for the process of the present invention include dinitroarylethers of the formula:

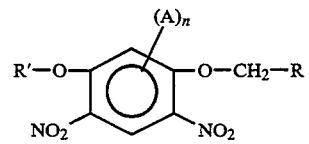

wherein R is hydrogen, $C_1-C_6$ alkyl, cycloalkyl or $CH=CH_2$; R' is hydrogen or $CH_2-R$; each A is independently Cl, Br, or I and n is 0, 1 or 2. Preferably n is 0; R is hydrogen or $C_1-C_6$ alkyl, and R' is hydrogen or $CH_2-R$. More preferably n is 0; R is methyl, ethyl, or hydrogen and R' is hydrogen. Most preferably n is 0 and R and R' are hydrogen.

The dinitroarylethers used can be prepared by techniques well-known in the art for preparing such ethers. Either a mono- or diether of 4,6-dinitroresorcinol can be used. In one embodiment, a monoether of 4,6-dinitroresorcinol can be advantageously prepared by contacting 1,3-dichloro-4,6-dinitrobenzene or 1,2,3-trichloro-4,6-dinitrobenzene with an aqueous hydroxy-containing compound in the presence of hydroxide base, preferably sodium hydroxide, under conditions sufficient to produce a monoether, specifically 5-alkoxy-2,4-dinitrophenol or 6-chloro-5-alkoxy-2,4-dinitrophenol. A diether of 4,6-dinitroresorcinol can be similarly prepared by contacting 1,3-dichloro-4,6-dinitrobenzene or 1,2,3-trichloro-4,6-dinitrobenzene with a hydroxy-containing compound in the presence of hydroxide base. (Greater amounts of hydroxy-containing compounds can be employed than in preparing the monoether.) Alternatively, the diether can be formed by contacting 1,3-dichloro-4,6-dinitrobenzene or 1,2,3-trichloro-4,6-dinitrobenzene with an alkanolic metal alkoxide, preferably methanolic sodium methoxide, under conditions sufficient to produce a diether, specifically 1,3-dimethoxy-4,6-dinitrobenzene or 1,3-dimethoxy-2-chloro-4,6-dinitrobenzene. 1,3-Dichloro-4,6-dinitrobenzene can be prepared by dinitrating m-dichlorobenzene as described in Boyer and Buriks, Organic Synthesis Collective Vol. 5, pg. 1067, John Wiley & Sons Inc. New York 1973 and 1,2,3-trichlorobenzene may be dinitrated under equivalent conditions.

The dinitroarylethers can be prepared using any hydroxy-containing compound which will form an ether when reacted with a dinitroaryl compound. The preferred hydroxy-containing compounds are cycloalkyl alcohols, branched- or straight-chain $C_1$-$C_7$ alkyl alcohols, and allyl alcohol. More preferred are alkyl alcohols, such as methanol and ethanol, with methanol being the most preferred.

The alkanolic metal alkoxide which can be employed in preparing the dinitroarylether is an alkanolic solution containing an alkali metal alkoxide which can be prepared by dissolving an alkali metal in an alkanol. The alkanol can be a $C_1$-$C_7$ alkanol, is preferably a $C_1$-$C_3$ alkanol and is most preferably methanol. The metal can be any alkali metal and is most preferably sodium. The solution may contain any effective amount of alkali metal but it preferably contains from about 20 to about 40, most preferably about 25 weight percent, said weight percent being based on the total weight of the solution.

In another embodiment, a monoether of 4,6-dinitroresorcinol can advantageously be prepared by contacting 1-chloro-2,4-dinitrobenzene with a hydroperoxide in the presence of an anhydrous alkali metal hydroxide, (as described in Makosza and Sienkiewicz, *Journal of Organic Chemistry*, Vol. 55 No. 17, Aug. 17, 1990, "Hydroxylation of Nitroarenes with Alkyl Hydroperoxide Artions via Vicarious Nucleophilic Substitution of Hydrogen"), and further reacted with an alkyl alcohol to form a 5-alkoxy-2,4-dinitrophenol.

The hydroperoxide may be any tertiary alkyl or aralkyl hydroperoxide. The term aralkyl refers to a radical in which an alkyl hydrogen atom is substituted by an aryl group. Preferred hydroperoxides are cumene, tert-butyl, and neopentyl hydroperoxides. More preferred are cumene hydroperoxide and tert-butyl hydroperoxide. Most preferred is cumene hydroperoxide.

The alkali metal hydroxide is preferably sodium hydroxide, potassium hydroxide, lithium hydroxide or cesium hydroxide. More preferred is sodium hydroxide or potassium hydroxide, wherein the most preferred is sodium hydroxide.

In the method of the present invention dinitroarylethers are reduced to form diaminoarylethers followed by an ether cleavage reaction to form diaminoresorcinol. Both the reduction and cleavage can be maintained within a single reaction vessel without isolation of intermediates, thus simplifying the reaction. Alternatively, but less preferably, the reactions can be conducted sequentially in two or more reaction vessels.

It is not particularly critical to the practice of the present invention how the reduction of the nitro groups of the dinitroarylethers is accomplished provided the desired number of the nitro groups are reduced to amino groups. Preferably, the reduction comprises contacting the dinitroarylether with hydrogen in the presence of a reduction catalyst.

The reduction catalyst can be any catalyst which will reduce the nitro groups to amines in the presence of hydrogen. Typical reduction catalysts include transition metal catalysts such as nickel, palladium, ruthenium and platinum. Preferably, the catalysts are supported, e.g., metal catalysts supported on carbon, and are palladium, ruthenium or platinum metal catalysts. The most preferred is palladium on carbon.

The amount of catalyst employed will depend on a number of factors including the specific catalyst selected. Typically, the catalyst is employed in an amount of about 0.1 to about 10 mole percent relative to the dinitroarylether. Preferably, the amount of catalyst employed is from about 2 to about 7, most preferably about 5 mole percent based on the amount of dinitroarylether.

The reduction reaction can be conducted at any temperature at which the reduction occurs and will depend upon a number of factors including the pressure and catalyst used. The pressure is not critical to the process of the present invention and any pressure may be used which will allow reduction to occur. Typically, atmospheric pressure is employed. The reaction is normally conducted at temperatures from about 20° C. to about 110° C. Preferably, the reaction is conducted at temperatures from about 40° C. to about 80° C., most preferably at temperatures from about 50° C. to about 60° C. The time required for the reduction reaction is also dependent upon the reaction conditions including temperature, pressure, catalyst used and desired conversion, but is generally the amount of time needed to convert substantially all the dinitroarylether to the diaminoarylether. In general the reaction requires from about 1 to about 10 hours for complete conversion. More preferably the reaction is conducted for about 2 to about 8 hours. Most preferably, the reaction is conducted for about 4 hours.

The catalytic reduction is preferably conducted in a solvent for the diaminoarylether. Preferred solvents include water and ethylene glycol. The most preferred solvent is water.

In addition, the reduction may also be carried out in the presence of a reducing agent such as stannous chloride, lithium aluminum hydride or any other reducing agents known in the art. The amount of these reducing agents used will depend upon the specific reducing agent and dinitroarylether used in the reduction reaction and will typically be at least the stoichiometric amount needed for the reduction reaction to occur.

The diaminoarylether product is preferably obtained as a hydrohalide salt by adding hydrohalide to the reduction reaction. The hydrohalide can be added at any time but is most preferably added after the reduction reaction has been initiated. Hydrohalides which can be used include hydrochloric, hydrobromic and hydroiodic acids, with the preferred being hydrochloric acid. The amount of hydrohalide used is the amount needed to obtain the desired hydrohalide salt. Preferably, at least 2 equivalents of hydrohalide are used in relation to the dinitroarylether.

Upon desired completion of the reduction reaction, the reduction catalyst is removed using conventional techniques such as filtration. The filtration may be conducted such that the filtrate is maintained within the same reaction vessel.

The ether cleavage reaction may be accomplished using any reagent which will cleave ethers from aryl compounds. These reagents include hydrochloric, hydrobromic or hydroiodic acids, lithium chloride, and tertiary amide hydrohalide salts, e.g., N,N-dimethyl acetamide or N-methylpyrrolidinone. Preferably the cleavage is accomplished by saturating the reaction mixture containing the diaminoarylether hydrohalide salt with dry HCl, adjusting the temperature to a sufficient amount and for a sufficient amount of time such that the ether group(s) are cleaved and 4,6-diaminoresorcinol is formed.

The cleavage reaction can be conducted at any temperature at which the cleavage will occur and will depend on a number of factors including the specific diaminoarylether used and reaction conditions. The reaction is generally conducted at a temperature from about 80° C. to about 200° C., more preferably at a temperature from about 120° C. to about 180° C., and most preferably from about 145° C. to about 165° C.

The pressure of the cleavage reaction is not critical and may be any pressure at which the cleavage reaction will occur. Typically, the pressure is from about 200 to about 500 psi. Most preferably the reaction is conducted at a pressure of about 350 psi.

The time necessary for the cleavage reaction to occur is also dependent upon the other reaction conditions, the specific diaminoarylether used and the desired conversions. In general the reaction is continued until substantially all the diaminoarylether has been converted to diaminoresorcinol. Preferably the reaction is conducted between about 12 to about 36 hours. More preferably the reaction is conducted between about 15 to about 24 hours. Most preferably the reaction is completed in about 18 hours.

4,6-Diaminoresorcinol is formed as a hydrohalide salt or other stabilized form thereof. Preferably 4,6-diaminoresorcinol is recovered as a hydrochloride, hydrobromide or hydroiodide salt. Most preferably 4,6-diaminoresorcinol is recovered as a hydrochloride salt.

The following examples are set forth to illustrate the present invention and should not be construed to limit its scope. In the examples, all parts and percentages are by weight unless otherwise indicated.

Preparing Ethers of Dinitroresorcinol

EXAMPLE 1

Preparing 5-Methoxy-2,4-dinitrophenol from 1,3-Dichloro-4,6-dinitrobenzene

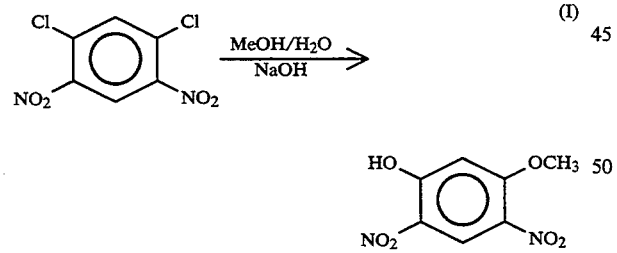

A 1 liter (L) round-bottom flask equipped with a mechanical stirrer and a reflux condenser is charged with 23.7 grams (g) of 1,3-dichloro-4,6-dinitrobenzene, 100 milliliters (mL) of methanol, 200 mL of water and 15 grams of sodium hydroxide and heated to approximately 65° C. for about 8 hours. The reaction mixture is then poured into 0° C. aqueous hydrochloric acid, isolated by filtration and air-dried. The theoretical yield of 5-methoxy-2,4-dinitrophenol, a monoether of dinitroresorcinol, is 21.4 g, and the dry weight yield is 20.5 g which gives an overall 95% yield of 5-methoxy-2,4-dinitrophenol.

EXAMPLE 2

Preparing 1,3-Dimethgxy-4,6-dinitrobenzene from 1,3-Dichloro-4,6-dinitrobenzene

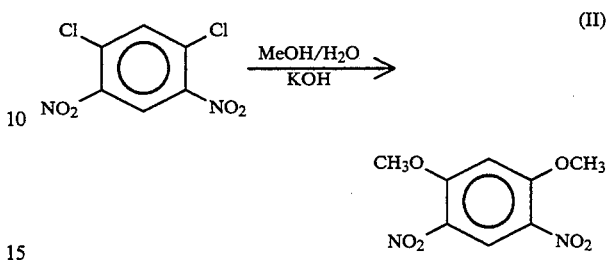

A 1-liter, 3-necked, round-bottomed flask is charged with 500 mL of methanol, 30 g of crushed potassium hydroxide, 75 mL of water, and 23.7 g (0.10 mole) of 1,3-dichloro-4,6-dinitrobenzene. The reaction mixture is agitated and heated to 65° C. for 8 hours and cooled to 25° C. The reaction mixture is then quenched with an excess of 0° C. aqueous hydrochloric acid. The resulting pale yellow solid is isolated by filtration and air-dried to yield 20 g (90% yield) of 1,3-dimethoxy-4,6-dinitrobenzene, a diether of dinitroresorcinol.

EXAMPLE 3

Preparing 5-Methoxy-2,4-dinitrophenol from 2,4-Dinitrochlorobenzene

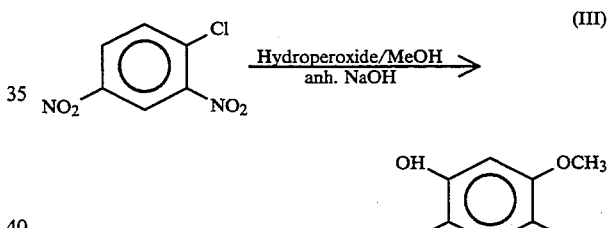

20 g of NaOH powder is added to a 250 mL 3-necked flask equipped with a mechanical stirrer, CO2 condenser, dropping funnel and thermowell. Approximately 100 to 125 mL of liquid NH3 are condensed into the reactor utilizing a dry ice bath. To the stirred slurry of powdered NaOH—NH3 a solution of 1-chloro-2,4-dinitrobenzene (0.1 mol) and cumene hydroperoxide (0.1 mol) in 50 mL of methylene chloride is added dropwise over 1 hour maintaining the temperature at −30° C. by the refluxing NH3.

After the addition is complete, the reaction mixture is allowed to warm to −10° C. to 0° C. and 75 mL of methanol containing 0.1 to 2 g of sodium hypophosphite is added dropwise over 1 hour. The resulting solution is agitated at room temperature for 3 to 4 hours.

The reaction mixture which contains precipitated Na phenolic salts is diluted with water to dissolve the salts and transferred to a 1-L separating funnel (to which a 500 mL solution of H2O has been added) where the aqueous solution is extracted with CH2Cl2 (2×200 mL) to remove the cumene derivatives. After extraction, the aqueous phenate salt solution is slowly acidified with concentrated HCl at a temperature of approximately 25° C. or less to precipitate the desired 5-methoxy-2,4-dinitrophenol, a monoether of dinitroresorcinol. The crude phenol (17 to 19 g) is recrystallized from H2O-

MeOH (50:50) to give 5-methoxy-2,4-dinitrophenol in 75% to 80% yield.

Preparing Diaminoarylethers from Dinitroarylethers

EXAMPLE 4

Preparing 5-Methoxy-2,4-diaminophenol Dihydrochloride from 5-Methoxy-2,4-dinitrophenol

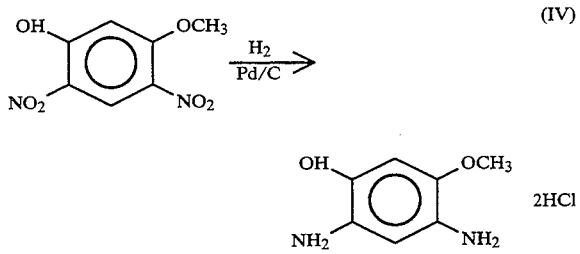

A 500 mL, 3-necked, round-bottomed flask is charged with 150 mL of water, 21.4 g (0.1 mole) of 5-methoxy-2,4-dinitrophenol and 1.0 g of 10% palladium on carbon catalyst. The reaction is stirred under a nitrogen atmosphere for 3 to 4 minutes. The stirred reaction mixture is heated to 55° C. and hydrogen gas is sparged below the surface of the reaction mixture. After 10 minutes, 19.8 g (0.2 mole) of concentrated HCl is added through the condenser while hydrogenation is continued for 4 hours. The catalyst is removed by filtration and the filtrate is passed into a solution consisting of 0.5 g of stannous chloride dihydrate and 25 mL of concentrated HCl. This solution is then saturated with dry HCl gas and cooled to 25° C. The solvent is then removed under reduced pressure (15 mm) to yield a pale, off-white solid. The product is then isolated as the dihydrochloride salt after drying in a vacuum oven for approximately 18 hours at 40° C., to give 5-methoxy-4,6-diaminophenol dihydrochloride (21.0 g, 92.5% yield).

Preparing 4,6-Diaminoresorcinol Dihydrochloride

EXAMPLE 5

Preparing 4,6-Diaminoresorcinol Dihydrochloride from 5-Methoxy-2,4-diaminophenol

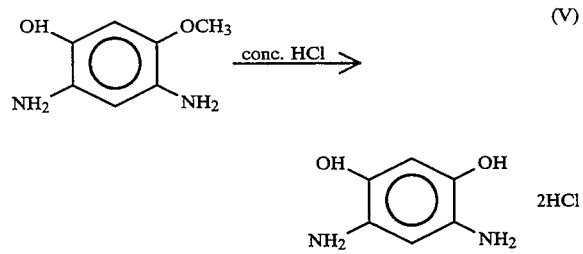

2.5 g of 5-methoxy-2,4-diaminophenol and 25 mL of concentrated HCl is placed in a 45 mL Hastalloy C autoclave. The mixture is then heated to 140° C. for 16 hours at a pressure of about 200 psi. The reaction mixture is then cooled to 25° C., the reactor is vented and the product, a white solid, is filtered and dried to yield 1.2 g of crude 4,6-diaminoresorcinol dihydrochloride.

EXAMPLE 6

Preparing 4,6-Diaminoresorcinol Dihydrochloride from 5-Methoxy-2,4-dinitrophenol

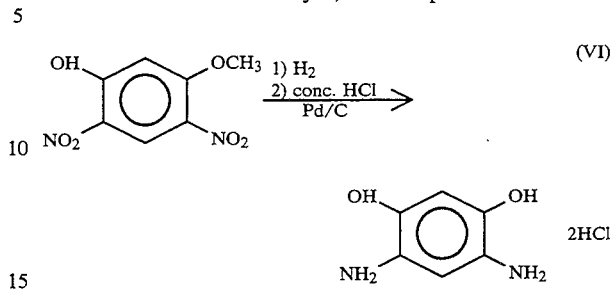

A 500 mL, 3-necked, round-bottomed flask is charged with 150 mL of water, 21.4 g (0.1 mole) of 5-methoxy-2,4-dinitrophenol and 1.0 g of 10% palladium on carbon catalyst. The reaction is stirred under a nitrogen atmosphere for 3 to 4 minutes. The stirred reaction mixture is heated to 55° C. and hydrogen gas is sparged below the surface of the reaction mixture. After 10 minutes, 19.8 g (0.2 mole) of concentrated HCl is added through the condenser while hydrogenation is continued for 4 hours. The catalyst is removed by filtration and the filtrate is passed into a solution consisting of 0.5 g of stannous chloride dihydrate and 25 mL of concentrated HCl. This solution is then saturated with dry HCl gas and charged to a 600 mL 5 Hastalloy B autoclave. The reactor is heated to 150° C. for 18 hours and cooled to 25° C. The resulting product is isolated by filtration and dried under nitrogen to yield 19.7 g (90% yield) of crude 4,6-diaminoresorcinol dihydrochloride.

What is claimed is:

1. A method for producing 4,6-diaminoresorcinol comprising
   a) reducing a dinitroarylether of the formula:

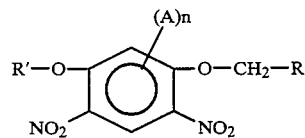

wherein R is hydrogen, $C_1$–$C_6$ alkyl, cycloalkyl or $CH=CH_2$, R' is hydrogen or $CH_2$—R, each A is independently Cl, Br, or I, and n is 0, 1 or 2; to form a diaminoarylether, and b) cleaving the ether group(s) from the diaminoarylether under conditions such that 4,6-diaminoresorcinol is formed as a salt or other stabilized form thereof.

2. A method of claim 1 wherein the dinitroarylether is reduced using hydrogen in the presence of a reduction catalyst.

3. A method of claim 2 wherein the catalyst is a nickel, palladium, ruthenium or platinum catalyst.

4. A method of claim 3 wherein the catalyst is palladium on carbon.

5. A method of claim 1 wherein the dinitroarylether is reduced using a reducing agent.

6. A method of claim 5 wherein the reducing agent is stannous chloride or lithium aluminum hydride.

7. A method of claim 1 wherein the ether(s) is cleaved using hydrobromic, hydrochloric or hydroiodic acid.

8. A method of claim 7 wherein the ether(s) is cleaved using hydrochloric acid.

9. A method of claim 1 wherein the temperature of Step a is from about 20° C. to about 110° C.

10. A method of claim 9 wherein n is 0, R is hydrogen, $C_1$–$C_6$ alkyl, cycloalkyl or $CH=CH_2$, and R' is hydrogen or $CH_2$—R.

11. A method of claim 10 wherein n is 0, and R and R' are hydrogen.

12. A method of claim 1 wherein and R and R' are hydrogen.

13. A method of claim 12 wherein the dinitroarylether is reduced using hydrogen in the presence of a reduction catalyst.

14. A method of claim 13 wherein the catalyst is palladium on carbon.

15. A method of claim 14 wherein the ether(s) is cleaved using concentrated HCl.

16. A method of claim 1 wherein the temperature of Step b is between about 85° C. and about 200° C.

* * * * *